United States Patent [19]

Fabinski

[11] Patent Number: 4,714,832
[45] Date of Patent: Dec. 22, 1987

[54] PHOTOMETER

[75] Inventor: Walter Fabinski, Kriftel, Fed. Rep. of Germany

[73] Assignee: Hartmann & Braun AG, Frankfurt am Main, Fed. Rep. of Germany

[21] Appl. No.: 753,659

[22] Filed: Jul. 10, 1985

[30] Foreign Application Priority Data

Jul. 18, 1984 [DE] Fed. Rep. of Germany ....... 3426472
Dec. 20, 1984 [DE] Fed. Rep. of Germany ....... 3446436

[51] Int. Cl.⁴ ........................................... G01N 21/35
[52] U.S. Cl. .................................. 250/343; 250/338; 250/344; 250/345
[58] Field of Search .................. 250/343, 338 PY, 345, 250/344, 338 GA

[56]  References Cited
U.S. PATENT DOCUMENTS

| 3,005,097 | 10/1961 | Hummel | 250/345 |
| 3,453,432 | 7/1969 | McHenry | 250/338 PY |
| 3,769,096 | 10/1973 | Ashkin et al. | 250/338 PY |
| 3,781,910 | 12/1973 | Herrmann | 250/343 |
| 4,044,251 | 8/1977 | Taylor et al. | 250/342 |
| 4,236,827 | 12/1980 | Horiba et al. | 250/343 |
| 4,258,260 | 3/1981 | Obara et al. | 250/338 PY |
| 4,499,378 | 2/1985 | Miyatake et al. | 250/343 |
| 4,605,313 | 8/1986 | Kebabian | 250/343 |

FOREIGN PATENT DOCUMENTS 13388  1/1979  Japan ................................. 250/345

Primary Examiner—Carolyn E. Fields
Attorney, Agent, or Firm—Ralf H. Siegemund

[57]  ABSTRACT

Photometer with at least one measuring beam traversing a space that contains measuring gas is improved by a solid state detector made of a foil which is specifically made of polyvinyl-idene-fluoride or polyvinyl-fluoride or polyvinyl-chloride, and having an area, being at least as large as the cross-sectional area of the radiation that leaves the measuring and gas containing chamber; a measuring signal is extracted from the foil. The foil is preferably blackened and has a thickness between 6–10 micrometers.

12 Claims, 5 Drawing Figures

PHOTOMETER

BACKGROUND OF THE INVENTION

The present invention relates to a photometer. German printed patent application No. 29 10 188 and German printed patent application No. 15 98 893 disclose photometers wherein light beams traverse a measuring cuvette or chamber as well as a reference cuvette or chamber and are received by a gas filled detector or receiver having a cross section equaling the sum total of the cross section of measuring and reference cuvettes or chambers. Also, photometers are known wherein light beams having passed through measuring and reference chambers are received by solid state detectors whose radiation receiving surface is significantly smaller than the cross section of measuring and reference chambers. Such solid state receivers have the disadvantage therefore, that unless optical ray concentrating or focusing devices are included in the systems only a portion of the radiation that has passed through the various chambers are in fact detected. On the other hand such optical focusing equipment or the like can be quite expensive which is a cost increasing factor if the entire radiation area involved is rather large. This is particularly the case if thermo i.e. infrared radiation is involved. Moreover it may not always be possible to concentrate the entire amount of radiation involved by optical means upon the receiver. On the other hand the solid state detectors or infrared receivers have the advantage over gas filled detectors, that their stability lasts longer because they never run empty.

British Pat. No. 979,850 discloses a gas analyzer using two measuring chambers being passed through by infrared radiation. The radiation leaving the measuring reference chambers are detected under utilization of a semi-transparent mirror, which is arranged obliquely to the radiation in question. This analyzer presupposes for proper operation that a part of the infrared radiation reaching the detector traverses the oblique mirror and at the end of the chamber the radiation reaches a photoelectric cell after having passed through a filter, while another portion of the radiation reaching the detection chamber is reflected at right angles, passes through a second filter and is received by a laterally arranged photoelectric cell. The filters in this case have to be dimensioned so that the particular output characteristics of the photoelectric cells being connected in a differential circuit provide a characteristic value which is indicative of the concentration of the measuring gas contained in the measuring chamber. This analyzer therefore is different in principle from the type of analyzer to which the invention pertains. It is therefore a task to be solved by the invention to provide a photometer for fluid analysis using a solid state receiver which receives reference and measuring beams after having passed through appropriate gas chambers.

It is therefore an object of the present invention to provide a new and improved photometer in which measuring and reference beams are to be detected by a solid state detector.

In accordance with the preferred embodiment of the present invention it is suggested to provide the photometer in such manner that immediately behind the measuring and reference chambers a foil of polyvinyl-idene-fluoride is provided as a solid state receiver having a light responsive surface which is as large as a cross section through the measuring chamber or chambers. Alternatively, polyvinyl fluoride or polyvinylchloride can be used as solid state detector foil.

As far as the invention is concerned, matching of the dimensions, permits immediately the possibility of most favorable optical coupling. The foil made of polyvinyl idene fluoride PVDF may, to the extent it is round have a diameter from 14 to 25 mm. Quite analogously to a conventional photometer being equipped with a gas filled detector, now there is the advantage that focusing on other concentration of the impinging radiation is no longer necessary but of couse the solid state device suggested here avoids the drawbacks of the gas filled photometers as outlined above. Rather, the photometer constructed in accordance with the invention combines the advantages of an opto-pneumatic detector with the advantages of a solid state receiver, while avoiding disadvantages of either.

In accordance with a further development of the invention, the foil of the stated type can be arranged in a gas filled receiver chamber which absorbs infrared radiation, and, therefore, upon receiving radiation the chamber can be pyroelectrically as well as piezoelectrically effective, whereby the pyroelectric effect is used to determine reference signals while the piezoelectric effect is used to determine the measuring component. The piezoelectric effect results from the optopneumatic effect of the device in accordance with the invention, which also produces the pyroelectrical effect.

The measuring and reference signals will be separated by the device in accordance with the present invention under utilization of two specific features and characteristics of the specific solid state devices which features in fact become effective in sequence, whereby the utilization of the new photometer permits insitu application for measurement.

The detector itself is comprised of a chamber which is filled with the type of gas whose concentration is to be measured and determined or a particular representative substitute or replacement gas is used bearing as far as relevant absorption characteristics are concerned a well defined and therefore quantitatively ascertainable relationship to analogous qualities of the measuring gas.

One side of the measuring chamber is closed through a window that is transparent to infrared radiation, so that the radiation can indeed enter the chamber. Between the radiation source and the various devices all designed to absorb radiation to one extent or another, but upstream from the measuring chamber there is provided a modulation device which periodically interrupts the radiation at a particular, predetermined frequency. Moreover, a selection filter chamber may be provided in the radiation path, of a single path device, somewhere in front of the detector and being filled with a gas of the receiving kind which can be periodically inserted into and pulled out from the radiation path. The frequency of the motion of the filter chamber is smaller than the modulator frequency just referred to. The radiation passing into the filter chamber and absorbed therein will not be absorbed in any downstream absorption path, nor from the gas in the receiver and measuring chamber. Radiation permitted to pass the filter chamber will reach the device in accordance with the invention, in order to produce a pyroelectric effect whose intensity is proportional to the impinging radiation. This pyroelectric effect serves as a reference signal for the photometer.

Whenever the beam is not intercepted by the filtering chamber, all of the radiation includes also the absorption range in the gas in the receiver chamber. Therefore the receiver absorbs radiation otherwise filtered out occurs and is in effect converted into pressure causing some deflection of the foil. The degree and magnitude of that deflection depends on the preabsorption in the absorption path. And therefore can be used for the formation of a measuring signal, particularly under utilization of the piezoelectric effect of the foil.

The detector in accordance with the invention can be used in a photometer, wherein the radiation leaving the radiation source, but prior to reaching the detection chamber passes through an absorption chamber, being flown through on a continuous basis by measuring gas. Alternatively, the invention is useable in photometers for insitu measurements whereby the flow of gas to be analyzed passes generally between the radiation unit and the receiver unit.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings in which:

Proceeding now to the detailed description of the drawings. FIGS. 1 and 2 illustrate a source 1 of infrared radiation, the radiation of which is in effect bi-parted into two paths, to establish two separate infrared light paths. A disk 3 is provided along its periphery as well as in a radially inner circle, concentrically thereto, with two marking tracks defined by transparent and opaque indicia or markers and being rotated by means of a motor 2. Therefore, the two light paths from the radiation source 1 are each alternatingly interrupted and not interruped, whereby the two marking tracks are 180 degree out of phase so that in fact the interruption of the radiation in the two light and beam path is in phase opposition.

Figure 1:
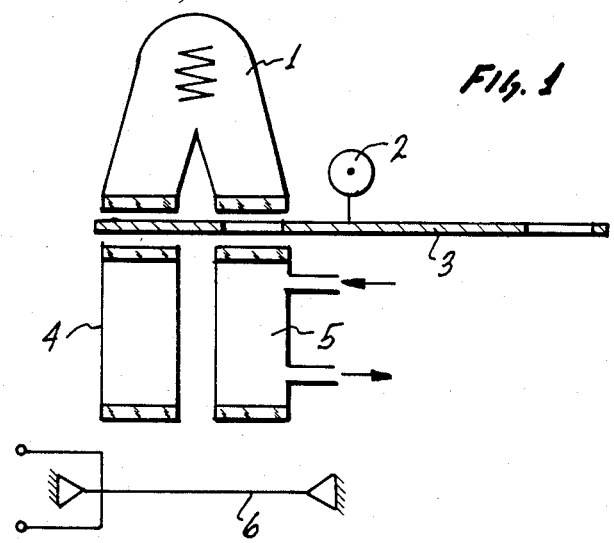
FIGS. 1 and 2 illustrate photometers, improved in accordance with the feature of the present invention, being provided with separate reference and measuring chambers.
Figure 2:
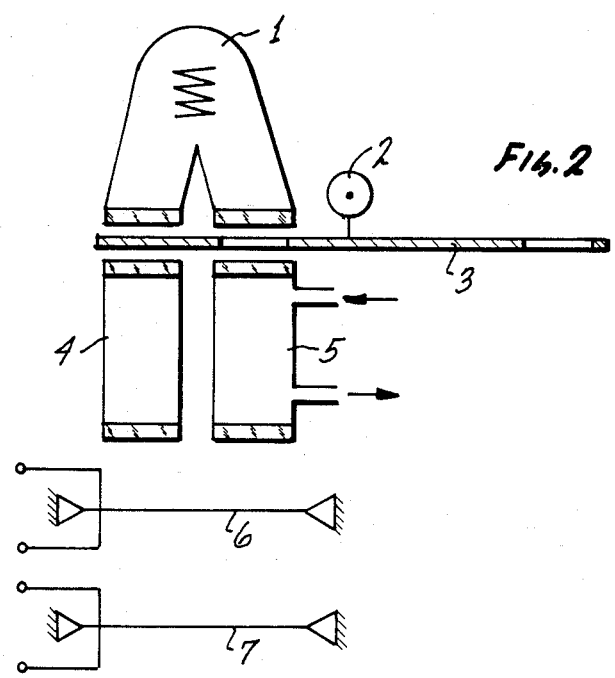

Still in those examples for FIGS. 1 and 2, there is a reference chamber 4 and a measuring chamber 5, respectively interposed in the two light paths. These chambers are equally long. Chamber 4 is closed and contains the reference gas on a permanent basis. Measuring chamber 5 is assumed to be flown through on a continuous basis by measuring gas.

Now in accordance with the preferred embodiment of the present invention, particular detectors are provided on the exit side of the two chambers 4 and 5. In particular FIG. 1 illustrates a foil 6 made of the PVDF material and covering in fact the entire aperture, as provided by the exit windows of the two chambers 4 and 5.

This particular PVDF foil 6 exhibits the above mentioned pyroelectric effect as well as the piezoelectric effect. Concerning the thermo effect the PVDF foil 6 is optimized through blackening of the surface facing the two chambers 4 and 5. The PVDF foil 6 has a thickness from 6 to 10 micrometers.

It was found that in lieu of the foil made of PVDF one can use a polymer with similar pyroelectric properties, such as polyvinyl fluoride or polyvinyl chloride.

The device in accordance with the invention compares favorably with photometers of the conventional type and using also solid state receivers, because in the device in accordance with the invention, the path length not flown through by measuring gas is very short. Longer path length could easily lead to faulty measurements particularly if the outer atmosphere contains also components of the measuring gas such as carbon dioxide or water; both of course are normally found in the atmosphere at least to some extent. If the photometer is subjected to shaking and shocks one should use a second foil 7 as is shown in FIG. 2. The two foils 6 and 7 are electrically connected in opposition to each other.

Figure 3:
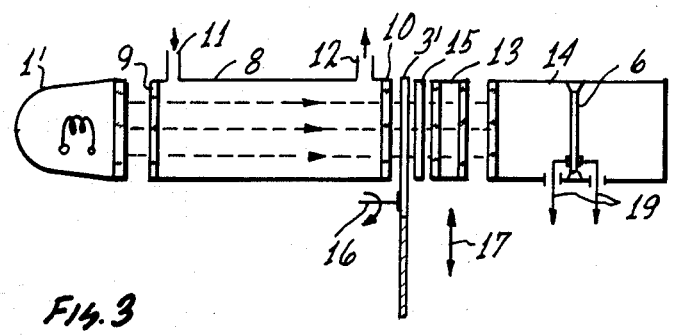
FIGS. 3 and 4 illustrate photometers likewise including the features of the invention, but using single beam operation and principle.

Proceeding now to the description of the photometer shown in FIG. 3, infrared radiation from a source 1' passes into an absorption chamber 8, having an entrance window 9 and an exit window 10 respectively at opposite ends and which are transparent to infrared radiation. The absorption chamber 8 is flown through by gas to be analyzed, there is an inlet 11 and an outlet 12 accordingly.

Radiation leaving the chamber 8 through the window 10 meets a solid state filter 15, and after passing through the filter a selective filter chamber 13 is passed through by the light; the chamber 13 contains the measuring gas component, pure or at a very high concentration. Whatever radiation is permitted to leave the chamber 13, will reach a receiver or detector chamber 14. This chamber is also filled with gas of the measuring gas variety. A modulating wheel 3' of the type explained above the reference to FIGS. 1 and 2 is interposed between absorption chamber 8 and filter 15, rotating about an axis 16. The modulating wheel 3' may be arranged instead directly in front of the radiation source 1, i.e. between source 1 and entrance window 9 of the chamber 8. In this respect then the arrangement would be analogous to the one shown in FIGS. 1 and 2.

Now in accordance with a particlar aspect of the invention, the selection chamber 13 is moved intermittently, as indicated by the arrow 17. In particular it is placed into the position shown in the drawing, or pulled out of that radiation path, so that the radiation from the filter 15 reaches directly the chamber 14.

Also as stated above the frequency of moving the chamber 13 in and out of the radiation path is smaller than the interruption pattern produced by modulator wheel 3' so that the latter modulation so to speak serves as a carrier and the back and forth movement of chamber superimposes a modulation upon such a carrier frequency. Typically, this carrier modulation (or, better, generation) occurs at a frequency between 5 and 20 cps; the frequency of moving the selection chamber 13 into and out of the ray path may be of the order of 1 cps or smaller.

The detection and receiver chamber 14 is filled with measuring component as mentioned, but contains in addition a foil of polyvinyl idene fluoride 6, which operates upon receiving radiation pyroelectrically as well as optic-pneumatically. A reference signal is produced as the immediate and direct consequence of the pyroelectric effect, while the piezoelectric effect of the foil is a consequence of the opto-pneumatical effect and results in measuring signals.

In accordance with a specific feature of the invention, the foil 6 is provided in this instance on both sides with a very thin transparent electrically conducting material, such as a very thin metal layer. These signals develop between these electrodes and are extracted from the receiver through electrical contact and lead out wires 19. The contact 19 electrically contacts the two electric layers on opposite surfaces of the foil 6, which of course are electrically insulated by the foil itself. In order to increase the pyroelectric effect, the foil 6 may moreover be blackened by a carbon black or the like on the side facing the radiation. The piezoelectric effect develops upon bending of foil 6 separating the interior of chamber 14 into a portion that absorbs radiation and a portion that does not, so that a pressure differential develops, bending the foil 6 which will develop a piezoelectric signal accordingly.

Figure 4:
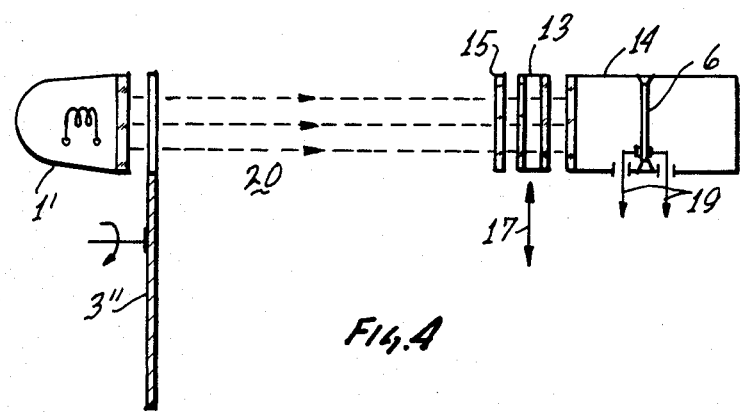

Proceeding to the description of FIG. 4, a photometer for so-called insitu measurements is shown here. Radiation source 1' is similarly to FIG. 3 and a wheel 3" being of the type shown in FIGS. 1 and 2 but with a single marking track is interposed, i.e. the markings pass right in front of the exit window of the radiation source 1 for a single beam modulation.

This embodiment differs from the embodiment in FIG. 3 by that modulation arrangement; moreover a gas flow 20 occurs somewhere in some fashion in the space between the wheel 3" on one hand, and the filter 15 on the other side, the gas flow path is otherwise not as well defined and confined as shown with reference to FIG. 3. On the other hand, the detection elements 15, 13, 14, 6 and 19 are all the same or similar as shown in FIG. 3.

The measuring effect as per FIGS. 3 and 4 is basically the result of the modulation produced by wheel 3' or 3", providing a carrier frequency type modulation as stated and interrupting the single beams in both cases. Preferably a frequency between 5 and 20 hertz was found suitable as carrier frequency.

Figure 5:
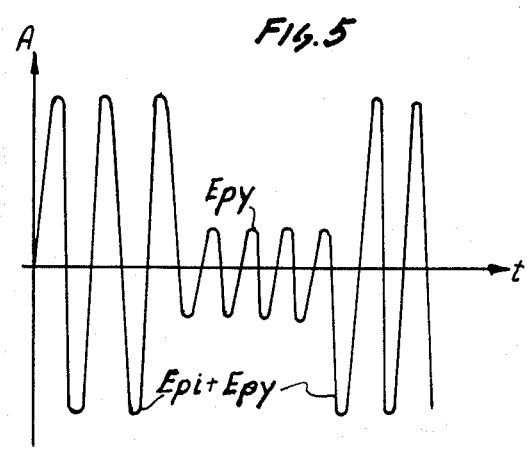
FIG. 5 is a diagram to more fully illustrate operation of and the measuring principle employed in the photometer shown in FIGS. 3 and 4.

FIG. 5 illustrates a representative example of the signal A which can be extracted from the electrodes and terminals 19, and as they are typically produced in a device of the type shown in FIGS. 3 and 4. If the photometer as per FIGS. 3 and 4 finds the selection chamber 13 extracted from the beam path the signal has relatively large amplitudes and in FIG. 5 the largest amplitudes can be deemed to represent this situation. This means then that the pyroelectric effect Epy is added to the piezoelectric effect Epi.

Now in accordance with the invention, the selection chamber 13 is shifted into the measuring path and signal drops; as indicated in FIG. 5 the smaller signal is now attributable only, or at least to a predominant extent only by the pyroelectric effect Epy. It can readily be seen moreover, that upon alternating the position of the selection chamber 13, one obtains an amplitude modulation of the basis signal in which in accordance with the rhythm of the placement of this selection chamber the amplitude assumes higher or lower values.

Particularly in case of low amplitude, the piezoelectric effect is substantially suppressed, and in this phase which is in the essence the phase in which the reference signal is formed, preabsorption occurs of relevant radiation portions inside the selection chamber 13. The absorbed component of course is missing from the radiation input in the chamber 14, and can therefore not contribute to the heating of the gas in the chamber 14.

The signals which can be represented as EPi alternating with Epy+Epi are extracted in that modulated fashion from the terminals 19 and are fed to an evaluating unit. The changeover of this evaluating unit can be synchronized mechanically or electrically to the movement of the selection chamber 13. In other words the two signal portions can readily be separated by a quasi demodulating effect that is synchronized to the modulation provided by the back and forth movement of the selection chamber 13.

The photometers in accordance with FIGS. 3 and 4 are additionally provided with interference filter 15. The passage range of the interference filter 15 should correspond to the absorption range of the measuring component. The interference filter 15 limits the load on the inventive foil 6 and as produced by the effective radiation. Moreover the interference filter permits elimination of errors that may result from companion gases which have also absorbtive properties and may falsify the gas concentration reading that is to be obtained by the apparatus as per the invention.

The evaluation of the electrical signal established by the circuit and as illustrated representatively in FIG. 5 can be carried out by simple computing operation. For example the measuring value EA can be extracted from the following algebraic combination $$EA = \frac{\text{alpha} \times Epi + Epy - \text{beta} \times Epy}{Epy}$$

wherein alpha represents the absorption of the measuring component and beta is a zero offset factor in order to adjust the zero position of the instrument.

The invention is not limited to the embodiments described above, but all changes and modifications thereof, not constituting departures from the spirit and scope of the invention, are intended to be included.

I claim:

1. Photometer including one measuring beam, traversing a chamber containing measuring gas, the improvement comprising a solid state detector positioned directly adjacent an exiting window of the chamber and being comprised of a foil made of polyvinyl-idene-fluoride, polyvinyl fluoride, or polyvinyl chloride and having an area being at least as large as the cross sectional area of radiation leaving said measuring chamber, and means for extracting a measuring signal from the foil.

2. Photometer in accordance with claim 1, said foil being blackened at a surface facing said radiation.

3. Photometer as in claim 1, said foil having a thickness between 6 and 10 micrometers.

4. Photometer as in claim 1, and including a second similar foil arranged behind the first mentioned foil.

5. Photometer as in claim 1, including separate measuring and reference beams respectively traversing measuring and reference gas chambers, said foil intercepting both beams; and means for modulating the beams in phase opposition.

6. Photometer, including at least one measuring beam traversing a measuring chamber containing measuring gas, the improvement comprising:
a solid state detector being comprised of a foil made of polyvinyl-idene-fluoride, polyvinyl fluoride, or polyvinyl chloride, and having an area being as large as a cross-sectional area of radiation leaving said measuring chamber;

said foil being contained in a gas-filled, infrared absorbing, receiving and detecting chamber, having a window facing said measuring gas containing chamber to receive therefrom radiation, the radiation received by and in said receiving chamber being pyroelectrically as well as piezoelectrically effective;

means for extracting a measuring signal from the foil; and means connected for separating a piezoelectric component from a pyroelectric component as contained in said mesuring signal.

7. Photometer as in claim 6, including means for amplitude modulating said radiation.

8. Photometer as in claim 7 and including a selection chamber means containing measuring component and alternatingly intercepting said beam to obtain a modulation of the carrier at a lower frequency.

9. Photometer as in claim 6, including a selection chamber means filled with measuring component for shifting in and out of beam path established between said measuring chamber and said receiving and detecting chamber.

10. Photometer including a single beam traversing a space containing or being passed through by a measuring gas, the improvement comprising:

a solid state detector being comprised of a foil made of polyvinyl-idene-fluoride, polyvinyl fluoride or polyvinyl-chloride;

said foil being placed on a beam exit side of the space and having an areal extension to be capable of capturing substantially all of the beams leaving said space;

a selection cell; means for alternatingly placing the selection cell into a path between the space and the detector, and removing the selection cell therefrom for alternatingly establishing the beam as leaving said exit side as a reference as well a measuring beam wherein the foil is pyroelectrically and piezoelectrically effective to provide reference and measuring signals.

11. Photometer as in claim 10, the cell being filled with the measuring component in the measuring gas.

12. Photometer as in claim 10, said detector foil being contained in a chamber filled with an infrared absorbing gas.

* * * * *